United States Patent
Sanchez Ramos et al.

(10) Patent No.: US 11,662,507 B2
(45) Date of Patent: May 30, 2023

(54) REFRACTIVE SURFACE FOR BLOCKING SHORT- AND MEDIUM-WAVELENGTH VISIBLE-SPECTRUM RADIATION THAT AFFECTS HUMAN PHYSIOLOGY

(71) Applicants: TECNOLOGÍA SOSTENIBLE Y RESPONSABLE SL, Madrid (ES); UNIVERSIDAD COMPLUTENSE DE MADRID, Madrid (ES)

(72) Inventors: Celia Sanchez Ramos, Madrid (ES); Nilo Garcia Manchado, Madrid (ES)

(73) Assignees: TECNOLOGÍA SOSTENIBLE Y RESPONSABLE SL, Madrid (ES); UNIVERSIDAD COMPLUTENSE DE MADRID, Madrid (ES)

( * ) Notice: Subject to any disclaimer, the term of this patent is extended or adjusted under 35 U.S.C. 154(b) by 165 days.

(21) Appl. No.: 17/341,292

(22) Filed: Jun. 7, 2021

(65) Prior Publication Data

US 2021/0325584 A1 Oct. 21, 2021

Related U.S. Application Data

(63) Continuation of application No. 15/748,607, filed as application No. PCT/ES2016/070586 on Jul. 29, 2016, now Pat. No. 11,054,557.

(30) Foreign Application Priority Data

Jul. 29, 2015 (EP) .................................... 15382396

(51) Int. Cl.
*G09G 3/00* (2006.01)
*G02B 5/22* (2006.01)
(Continued)

(52) U.S. Cl.
CPC .............. *G02B 5/223* (2013.01); *A61F 9/065* (2013.01); *G02C 7/104* (2013.01); *G09G 3/00* (2013.01); *G02C 2202/10* (2013.01)

(58) Field of Classification Search
CPC ........................................................ G09G 3/00
See application file for complete search history.

(56) References Cited

U.S. PATENT DOCUMENTS

| 8,360,574 B2 | 1/2013 | Ishak et al. |
| 2008/0112069 A1 | 5/2008 | Helber et al. |

(Continued)

FOREIGN PATENT DOCUMENTS

| CN | 1137883 A | 12/1996 |
| EP | 2937911 A1 | 10/2015 |

(Continued)

OTHER PUBLICATIONS

Behar-Cohen et al. "Light-emitting 15 diodes (LED) for domestic lighting: Any risks for the eye?" Progress in Retinal and Eye Research 30 (2011)239-257] (19 pages).

(Continued)

*Primary Examiner* — Samantha (Yuehan) Wang
(74) *Attorney, Agent, or Firm* — Intellectual Property Law Group LLP

(57) ABSTRACT

The invention relates to a refractive surface for blocking short- and medium-wavelength visible-spectrum radiation that affects human physiology. The refractive surface selectively absorbs short wavelengths between 380 nm and 500 nm, between a maximum and a minimum absorption threshold, and selectively absorbs medium wavelengths between 500 nm and 590 nm, between a maximum and a minimum absorption threshold, the selective absorption of short and medium wavelengths between 380 nm and 590 nm not completely blocking the passage of visible light in this (Continued)

range. Other embodiments include an LED screen, a software product and an electronic device, and ophthalmic, intraocular or sunglass lenses.

22 Claims, 7 Drawing Sheets

(51) Int. Cl.
*A61F 9/06* (2006.01)
*G02C 7/10* (2006.01)

(56) References Cited

U.S. PATENT DOCUMENTS

| | | | |
|---|---|---|---|
| 2012/0001960 A1* | 1/2012 | Herz | G06F 1/3265 345/102 |
| 2012/0019493 A1* | 1/2012 | Barnhoefer | H05B 41/3922 345/207 |
| 2013/0141693 A1 | 6/2013 | McCabe | |
| 2014/0061689 A1* | 3/2014 | Seibel | H01L 25/0753 257/E33.068 |
| 2015/0287389 A1* | 10/2015 | Mese | G09G 5/10 345/207 |
| 2015/0338561 A1* | 11/2015 | Moe | G02B 5/208 156/60 |

FOREIGN PATENT DOCUMENTS

| | | |
|---|---|---|
| ES | 2247946 | 3/2006 |
| ES | 2257976 | 8/2007 |
| ES | 2281301 | 9/2007 |
| ES | 2281303 | 9/2007 |
| ES | 2289957 | 2/2008 |
| ES | 2296552 | 4/2008 |
| ES | 2298089 | 5/2008 |
| ES | 2303484 | 8/2008 |
| ES | 2312284 | 2/2009 |
| ES | 1094781 U | 12/2013 |
| GB | 1480492 A | 7/1977 |
| WO | WO 90/05321 A1 | 5/1990 |
| WO | WO 91/04717 | 4/1991 |
| WO | WO 98/44380 | 10/1998 |
| WO | WO 2014096475 A | 6/2014 |

OTHER PUBLICATIONS

Cajochen et al. "Evening exposure to a light-emitting diodes (LED)-backlight computer screen affects circadian physiology and cognitive performance", Journal of Applied Physiology 110: 1432-1438, 2011, first published Mar. 17, 2011 (7 pages).
International Search Report, dated Nov. 21, 2016 for corresponding International Application No. PCT/ES2016/070586 with English translation (5 pages).
Written Opinion of the ISA, dated Nov. 21, 2016 for corresponding International Application No. PCT/ES2016/070586 (5 pages).

* cited by examiner

REFRACTIVE SURFACE FOR BLOCKING SHORT- AND MEDIUM-WAVELENGTH VISIBLE-SPECTRUM RADIATION THAT AFFECTS HUMAN PHYSIOLOGY

CROSS-REFERENCE TO RELATED APPLICATIONS

This application is a continuation application of a co-pending U.S. patent application having a Ser. No. 15/748,607, filed on Jan. 29, 2018, which is a U.S. National Phase application, under 35 U.S.C. § 371, of International Application no. PCT/ES2016/070586, with an international filing date of Jul. 29, 2016, and claims benefit of European Application no. 15382396.8 filed on Jul. 29, 2015, each of which are hereby incorporated by reference for all purposes.

BACKGROUND OF THE INVENTION

1. Field of the Invention

The present invention falls within the general field of preventive medicine and public health and in particular relates to a diopter configured to restrict the radiations with short and medium wavelengths comprised between 380 and 590 nm. Objects of the present invention are also a method for blocking radiations with short and medium wavelengths and different types of devices also configured for blocking radiations with short and medium wavelengths affecting the human physiology such as for example the visual and non-visual function, sleep or food disorders, or any other where light is involved.

2. Background

The electromagnetic spectrum (EME) is the energy distribution of the whole of the electromagnetic waves that a substance emits (emission spectrum) or absorbs (absorption spectrum). The EME includes a wide range of radiation, from that of lower wavelength such as gamma rays and x-rays, passing through ultraviolet radiation, light and infrared rays (IR), to the electromagnetic waves with longer wavelength, such as radio waves.

The wavelengths in the range from 180 to 380 nm can cause photokeratitis and opacities in the crystal lens. In the range from 380 to 500 nm in the visible spectrum (violet and blue light) they can cause photomechanic, photothermal injuries and injuries to the retina (in the aphakic eye the range is increased from 310 nm to 500 nm). The heating by absorption of visible radiation or IRA (380-1200 nm) may also contribute to the formation of opacities in the crystal lens. In addition erosions may occur on the cornea. As a result of the transparency of the ocular means, visible radiation and IRA (380 to 1,400 nm) can cause thermal damage to the retina. In the range of the IR A and B (800 to 3,000 nm) the thermal lesions of the crystal lens are attributed to a degradation of crystalline proteins. In the region of the IR B and C of the spectrum (1,400 to 3,000 nm and 3,000 to 10,000 nm, respectively), absorption mainly occurs in the cornea and aqueous humor. Generally above 1,900 nm, the cornea is the only absorbent medium, by which thermal injuries are usually limited to this structure. This type of injury is almost exclusively due to exposure to laser radiation.

The light spectrum is the region of the electromagnetic spectrum that human eye is able to perceive. Electromagnetic radiation in this range of wavelengths is also called 'visible' or simply light. There are no exact limits in the visible spectrum; a typical human eye responds to wavelengths from 380 nm to 780 nm, although the eye adapted to the dark can see over a greater range, ranging from 360 nm to 830 nm.

The retina auto-protects itself from the short and medium wavelengths in two ways: with a heterogeneous distribution of the photo-receptors in such a way that photo-receptors, sensitive to the short wavelengths, do not exist in the macular depression and by the action of yellow pigments existing in the same area that also perform a protective action. In addition, the crystalline increases its proportion of chromophores with age. These natural protections of the human eye against the more energetic wavelengths (the crystalline and those of the retina) can find themselves seriously affected by certain pathologies and/or surgical interventions, even exclusively over time.

Some techniques have been developed to protect to healthy eyes, cataracts operated eyes and eyes on retinal neurodegenerative processes from the short wavelengths such as, for example, applying filters to the human eye as a therapeutic and preventive measure to replace and/or improve the natural protection. Since the middle of the 90's, intraocular lenses provided with a yellow filter have been implanted on cataract operated eyes. This alternative involves a surgical procedure with all its risks and difficulties. There also exist a large number of people operated from cataracts to which a transparent intraocular lens has been implanted to substitute the inner substance of the crystalline that does not have the necessary protection by the absence of pigmentation. In these cases, it is necessary to complement the artificial crystalline, which is exempt of pigmentation, with the insertion of a pigmentation support system.

The present invention provides a diopter configured to block the harmful short and medium wavelengths to the visual system comprised within the range of 380-590 nm. This diopter, which is understood as an element with a refractive surface, i.e., is a surface separating two means of different refractive index [*Manual de Optica Geometrica, Felipe*, 1998]. The diopters can be designed for the selection of a particular range of wavelengths of light.

There are different types of filters applied to the human eye on the market. For instance, the patent application WO 98/44380 describes a filter applied in a contact lens that does not cover the whole of said contact lens, understanding the whole as iris area, pupil area and the contact lens body, this fact being fundamental for avoiding irregularities in vision. On the other hand, the document WO 91/04717 describes intraocular lenses for treating of AMD which is not the object of the present invention. It is also known the fact of using yellow filters in ophthalmic lenses, for example through the document GB 1 480 492. The yellow filter can be used in multiple applications, as shown by the documents located in the current state of the art.

The document WO 90/05321 describes a filter with a series of technical features but that absolutely defines a pathophysiological application and in addition, the filter described in the patent application WO 90/05321 is not homogeneous in its absorbance, and may produce unwanted effects.

Dr. Celia Sanchez-Ramos is the inventor of the patents ES2247946, ES2257976, ES2281301, ES2281303, ES2289957, ES2296552, ES2298089, ES2303484 and ES2312284. However, although these documents are referred to the issue of ambient light with short wavelengths on the spectrum from 380 to 500 nm, in none of these documents the problem derived from the medium wavelengths ranging between 500 and 590 nm is envisaged, explained, suspected or raised.

FIG. 1 of the present document shows the different graphs of emission for consumer electronics currently marketed within the visible range. FIG. 2 shows the graph with the percentage of transmittance of the crystal lens depending on the age taken from [BRAINARD, G. C. et al. "Action spectrum for melatonin regulation in humans: Evidence for a novel circadian photoreceptor", Journal of Neuroscience (2001)]. More specifically, FIG. 2 shows the following data (table 1):

TABLE 1

| Wavelength | 0-9 years (% transmittance) | 20-29 years (% transmittance) | 60-69 years (% transmittance) |
|---|---|---|---|
| 400 nm | 20 | 10 | 2 |
| 425 nm | 70 | 50 | 10 |
| 450 nm | 88 | 68 | 30 |
| 475 nm | 90 | 78 | 45 |
| 500 nm | 92 | 88 | 40 |
| 525 nm | 95 | 80 | 68 |
| 550 nm | 95 | 80 | 75 |

Therefore, it is necessary a diopter that also takes into account these percentages of transmittance to avoid damage in the user's eye system, taking into account factors such as age, which is essential in this factor. For example, it is noteworthy that BRAINARD does not consider two groups of high risk: the range between 10-20 years old, where currently there is intensive use of LED screens that particularly affect the user's visual system (as described in PCT/ES2013/070222) or those over the age of 69, which is a group particularly sensitive to retinal damage by the metabolic changes due to age.

It is clear that today any particular user spends an average of 4-8 hours a day, or more, in front of LED-type displays, i.e. receiving an emission of short wavelengths at a usually very small distance (on the order of 30-50 cm), which negatively affects the eye and human vision. This issue is added to the problem described in the state of the art in [Behar-Cohen et al. "Light-emitting diodes (LED) for domestic lighting: Any risks for the eye?" Progress in Retinal and Eye Research 30 (2011)239-257]. Said document, in the conclusions thereof, emphasizes the need to evaluate the potential toxicity of the light emitted by the LEDs, depending on the various devices available on the market so that efficient recommendations can be made to the domestic light manufacturers, due to the increased presence of LED-type lighting for indoor environments. However, this document does not commit to a solution to combine the evolution of the LED technique with a risk-free everyday use. That is, this document advocates, directly, the limitation and legal regulation of light emissions, without proposing any kind of solution for the already marketed products.

Another document that describes the problems associated with the excessive exposure to light in [Cajochen et al. "Evening exposure to a light-emitting diodes (LED)-backlight computer screen affects circadian physiology and cognitive performance", Journal of Applied Physiology 110: 1432-1438, 2011, first published 17 Mar. 2011] where the need to adapt the blue light emission to the sleep cycle is described. This document, however, indicates that the potential toxicity of the LED-type displays is unknown and that, in any case, their associated problems can be reduced by reducing the light intensity which is not fully effective.

The technical problem described above underlies the reduction of risk in the eye damage due to the intensive use of LED-type displays. From the document by Behar-Cohen, it is known to which type of damages the human eye is exposed, but in its conclusions, the most obvious way is used, which is to limit the use of that type of screens and force manufacturers, in a generic way, to restrict their emissions. However, it leaves unanswered precisely how to reduce this type of emissions in the simplest way as possible, not only at the manufacturing step, which is not always possible, easy or simple, but also with the products currently existing on the market.

The problems described above are solved in the document PCT/ES2013/070222 considered as the state of the art closest to the present invention. Said document describes the degree of toxicity of the short wavelengths produced by LED light of different spectral composition (tests described below with reference to FIGS. 3-6 of the present document). In all cases, the test have been made for filtering short wavelengths comprised between 380-500 nm obviating other ranges that, as indicated, also affect retinal cell death and that therefore should be also solved, given the intensive use currently made of all types of light sources and display screens.

The specific objectives of the toxicity test and the solution provided by the document PCT/ES2013/070222 are as follows:
  a) Studying the cell viability of the retinal tissue in vitro after exposure to different LEDs that emit radiation of different spectral composition, as shown in FIG. 4.
  b) Assessing the DNA damage of the retinal tissue in vitro after exposure to different LEDs that emit radiation of different spectral composition, as shown in FIG. 5.
  c) Determining the apoptosis of the retinal tissue in vitro after exposure to different LEDs that emit radiation of different spectral composition, as shown in FIG. 6.

Following the assessment and determination of toxicity, the solutions proposed in the document PCT/ES2013/070222 are assessed. In this document, a lighting device was designed comprising six differentiated lighting zones separated off from each other by discriminating barriers of a white material. Each one of the zones contains a LED producing light with irradiance 5 mW/cm$^2$ but emitting light with different spectral composition:
  Blue LED (468 nm)
  Green LED (525 nm)
  Red LED (616 nm) White LED; Color T°=5400° K The lighting device used was placed on a culture plate, and the cells were exposed to LED light for 3 light-dark cycles (12 hours/12 hours) with and without the interposition of the blocking element of short wavelengths. There is a zone not illuminated by LED where the cells not exposed to light which were used as negative control are placed.

In this particular embodiment of the document PCT/ES2013/070222, the blocking element is defined as a blocking element of short wavelengths consisting of a substrate with a yellow pigment evenly distributed on its surface and, in that said pigment has an optical density such that it allows the selective absorption of short wavelengths between 380 nm and 500 nm within a range between 1 and 99%. More specifically, it is a film or multilayer film, where one of them is pigmented.

The retinal pigment epithelial cells (RPE) were thawed following the supplier's instructions, in "Epithelial cell culture medium", supplemented with fetal bovine serum (FBS) and growth factors. At 72 hours and once the culture reaches the confluence, the cells were raised with trypsin- EDTA and were seeded at a density of 5000 cells/well in a 96-well plate previously treated with poly-lysine. The culture was kept for 24 hours after which the medium was replaced by fresh medium (300 µl/well). This procedure was repeated each of the days in which the experiment was carried out to avoid evaporations by the heat produced by the lamps. The plate with the lighting device was placed within the incubator at 37° C. in an atmosphere of 5% CO2.

The toxicity experiment was conducted after the cells were incubated in the presence of light of different spectral characteristics for three exposure/rest cycles of twelve hours per cycle.

The samples were washed with PBS and fixed with 4% paraformaldehyde for 15 minutes. After fixation, the cells were permeated with 0.3% Triton for 10 minutes. Once the samples were permeated, they were blocked with 5% BSA and the anti-caspase and anti-H2AX antibodies dissolved in 2.5% PBS+BSA were then added at a concentration of 1:400 for the determination of apoptosis and DNA damage respectively.

After an hour of incubation, the samples were washed with PBS, and secondary antibodies, Alexa 594 and Alexa 633, were added at the same concentration as the primary antibody and incubated for additional 30 minutes. After incubation, the samples were washed and the signal was read in the BD Pathway 855 fluorescence microscope. For the activation of caspases, images were captured at 633 nm of emission and for H2AX at 594 nm.

Each experiment was repeated at least twice. The values are given as mean±standard deviation. The data were analyzed by statistical unpaired Student's t-test using the statistical software Statgraphics version Centurion XVI.I (USA). P-values of less than 0.05 were considered to be significant.

After a period of three light exposure cycles to for twelve hours, alternating with three recovery cycles for a further twelve hours, the nuclei of the primary human retinal pigment epithelial cells were DAPI-stained to count the number of cells per well.

The non-irradiated cells grew well in the wells, but irradiation with monochromatic LED light inhibited cell growth. Blue light (468 nm) produced a very significant reduction in the number of cells, although there was also an observable phototoxic effect for green light (525 nm); however in this document, this fact was not considered as relevant. In the case of white light (T°=5400° K) no statistically significant differences were observed.

A blocking element is designed to reduce emissions of shortwave without taking into account the phototoxic effect of green light (i.e. medium wavelengths). With the presence of the blocking element of short wavelengths (range 380-500 nm), an increase of cell viability was observed, mainly in cells exposed to white light (T°=5400° K) and light blue (468 nm) as shown in the table 2.

TABLE 2

| Cell viability | Control | White LED (T° = 5400° K) | Blue LED (458 nm) | Green LED (525 nm) | Red LED (616 nm) |
| --- | --- | --- | --- | --- | --- |
| Without blocking element (FU) | 855 ± 403 | 217 ± 108 | 10 ± 2 | 99 ± 114 | 339 ± 1 |
| With blocking element (FU) | 1156 ± 156 | 346 ± 71 | 358 ± 20 | 188 ± 43 | 420 ± 69 |

TABLE 2-continued

| Cell viability | Control | White LED (T° = 5400° K) | Blue LED (458 nm) | Green LED (525 nm) | Red LED (616 nm) |
| --- | --- | --- | --- | --- | --- |
| p-value | 0.212 | 0.047* | 0.000* | 0.102 | 0.096 |
| Increase (%) | — | 59 | 3480 | — | — |

In FIG. 4, the LED light effect and the photoprotective effect of a blocking element that selectively absorbs the short wavelengths on the cell viability in human retinal pigment epithelial cells can be seen. FU means fluorimetric unit, wherein it can be seen that the greatest protection is between 380-500 nm, not establishing any additional protection to the range between 500 and 590 nm. Significant differences in cell viability are not found since the blocking element was designed only to absorb short wavelengths 380-500 nm.

To examine whether the radiation had some effect on the integrity of cellular DNA, cells were marked using H2AX antibody. H2AX is a variant of the histone H2A that is involved in DNA repair, i.e. when there is damage in nuclear DNA. When the double-stranded DNA break occurs, H2AX histone is rapidly phosphorylated on serine 139 by kinase ATM and becomes Gamma-H2AFX. This phosphorylation step can extend to several thousands of nucleosomes from the site of the double-strand break and can mark the surrounding chromatin in the recruitment of the proteins necessary for damage signaling and DNA repair. As part of post-translational modifications of apoptosis, caused by severe DNA damage, a high expression of phosphorylated H2AX is considered as an accurate indicator of apoptosis. The results of experiments showed that anti-H2AX antibody recognizes sites of phosphorylated histones after irradiation with LED light indicating an activation of DNA repair mechanisms.

By interposing a blocking element of the short wavelengths, a significant decrease in activation of histone H2AX, indicative of less DNA damage, was observed. This decrease was 97% for white (T°=5400° K), blue (468 nm), and green (525 nm) LED light, and 95% in cells exposed to red LED light. As seen in table 3.

TABLE 3

| Activation of H2AX | Control | White LED (T° = 5400° K) | Blue LED (468 nm) | Green LED (525 nm) | Red LED (616 nm) |
| --- | --- | --- | --- | --- | --- |
| Without blocking element (FU) | 131 ± 41 | 2697 ± 493 | 2537 ± 589 | 2258 ± 738 | 1920 ± 286 |
| With blocking element (FU) | 47 ± 1 | 83 ± 20 | 76 ± 7 | 63 ± 10 | 91 ± 15 |
| p-value | 0.024* | 0.000* | 0.002* | 0.001* | 0.000* |
| Decrease (%) | — | 97% | 97% | 97% | 95% |

FIG. 5 shows the LED light effect and the photoprotective effect of a blocking element that selectively absorbs the short wavelengths on the activation of histone H2AX in human retinal pigment epithelial cells. FU means fluorescence unit.

The activation of caspase-3 and -7 was determined, since these enzymes are involved in the regulation and execution of apoptosis. The cells were marked using the anti-caspase antibody. Irradiation with LED light in the cells caused an increase in the percentage of apoptotic cells in the culture. The caspase activation is observed as a pinkish color around the blue-stained nucleus (DAPI).

The interposition of the blocking element of short wavelengths between 380-500 nm induced a significant decrease in caspase activation, indicative of apoptosis in cells exposed to the different LED light sources. This decrease was 89% for white (T°=5400° K) and blue (468 nm) lights, 54% for green light (525 nm), and 76% for red light, as shown in table 4.

TABLE 4

| Activation of caspases | Control | White LED (T° = 5400° K) | Blue LED (468 nm) | Green LED (525 nm) | Red LED (616 nm) |
|---|---|---|---|---|---|
| Without blocking element (FU) | 0.037 ± 0.02 | 0.888 ± 0.02 | 0.861 ± 0.03 | 0.839 ± 0.05 | 0.655 ± 0.07 |
| With blocking element (FU) | 0.114 ± 0.15 | 0.094 ± 0.03 | 0.094 ± 0.05 | 0.386 ± 0.48 | 0.155 ± 0.08 |
| p-value | 0.541 | 0.000* | 0.000* | 0.312 | 0.006* |
| Reduction (%) | — | 89% | 89% | 54% | 76% |

FIG. 6 shows the LED light effect and photoprotective effect of a blocking element that selectively absorbs the short wavelengths between 380-500 nm on the activation of the caspase-3, -7 in human retinal pigment epithelial cells. FU means fluorescence unit. Following an analysis of the problem and an example of solution, the light, especially that of smaller wavelengths, in 3 cycles of 12 hours of exposure alternating with 12 hours of recovery, affects the growth of the human retinal pigment epithelial cells. An increase in the number of cells expressing the histone H2AX (DNA damage) y caspase-3 and -7 (apoptosis) occurs.

In all cases the blocking element described in PCT/ES2013/070222 that selectively absorbs the short wavelengths between 380-500 nm exerts a protective effect against the damaging effects of light on the human retinal pigment epithelial cells. However, said document does not recognize the problems associated with apoptosis and retinal cell death in the range comprised between 500-590 nm, as can be seen perfectly in the FIG. 6 where within that range the fluorimetric intensity (FU) in the case of using a filter as described in PCT/ES2013/070222 is 54% indicating a high cell death far exceeding even that occurs in the range above 590 nm.

It is therefore an object of the present invention to improve the survival rate in the range of 500 to 590 nm (i.e. medium wavelengths) where mortality is higher than in the rest of the ranges after filtering the short wave. For example, the filter used in the document PCT/ES2013/070222 does not seek the reduction of mortality in 618 nm, but it is achieved (76% survival) with much less of an impact on the previous range (in the green survival is only 54%). Therefore, there is a need for a solution which, in addition to the above (reduction of mortality in the range of the blue and red), reduces mortality in the range of 500 to 590 nm. This implies that an empirical observation of the mechanisms that affect cell mortality in the different ranges (blue, green and red) not described in the above document is required.

Therefore, and given that the cell death within that range (500-590 nm) is very high even incorporating a blocking element within the range 380-500 nm as described in PCT/ES2013/070222, the introduction of a diopter is required to mitigate these adverse effects in said range and complementary with the advantages of the blocking element described in the document PCT/ES2013/070222.

SUMMARY OF THE INVENTION

It is an object of the present invention a diopter for blocking short wavelengths comprised between 380 and 590 nm having different aspects and embodiments, all of them linked by the common inventive concept of blocking the short and medium wavelengths comprised in the cited ranges of the visible light spectrum.

The technical problem which the present invention solves is the reduction of risk in the eye damage in the user's visual system, especially due to the intensive use of display screens used in electronic devices. This technical problem is resolved by different aspects of the invention such as a diopter, a blocking method, a computer-implemented blocking method, a screen incorporating the diopter, a method for manufacturing and a portable electronic device configured for blocking short wavelengths according to independent claims accompanying the present specification and hereby incorporated by reference thereto. Particular embodiments of the different aspects of the invention are described in dependent claims and are also incorporated in this description by reference.

The inventive concept common to all the different aspects and embodiments of the present invention is, precisely, blocking the short and medium wavelengths between 380-590 nm. Document PCT/ES2013/070222 comprises the protection between 380 and 500 nm and it is necessary to extend protection to 590 nm without distorting the protection in the previous range. This extension allows increasing further the life of retinal cells, improving user's eye system in all short and medium wavelength ranges.

Throughout the description and claims, the word "comprises" and its variations are not intended to exclude other technical features, additives, components or steps. For those skilled in the art, other objects, advantages and characteristics of the invention will emerge in part from the description and in part from the practice of the invention. The following examples and drawings are provided by way of illustration, and are not intended to be limiting of the present invention. Furthermore, the present invention covers all the possible combinations of particular and preferred embodiments herein indicated.

BRIEF DESCRIPTION OF THE DRAWINGS

Described very briefly hereinafter are a series of drawings that help to better understand the invention and which are expressly related to an embodiment of said invention that is presented as a non-limiting example thereof.

DETAILED DESCRIPTION OF SPECIFIC EMBODIMENTS

Figure 1:
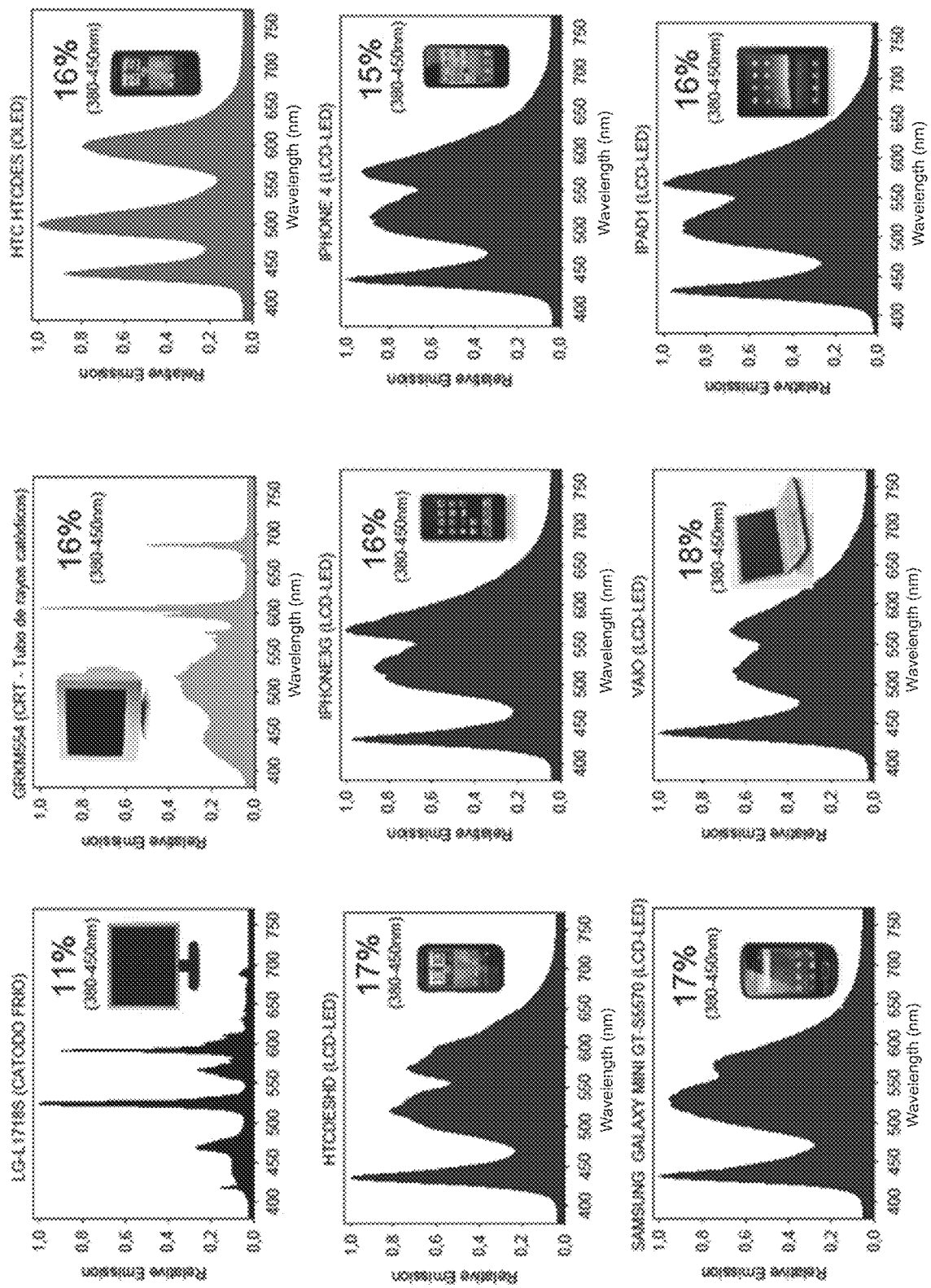
FIG. 1 shows different graphs of emissions for commercial electronic products with LED-type display described in the current state of the art.
Figure 2:
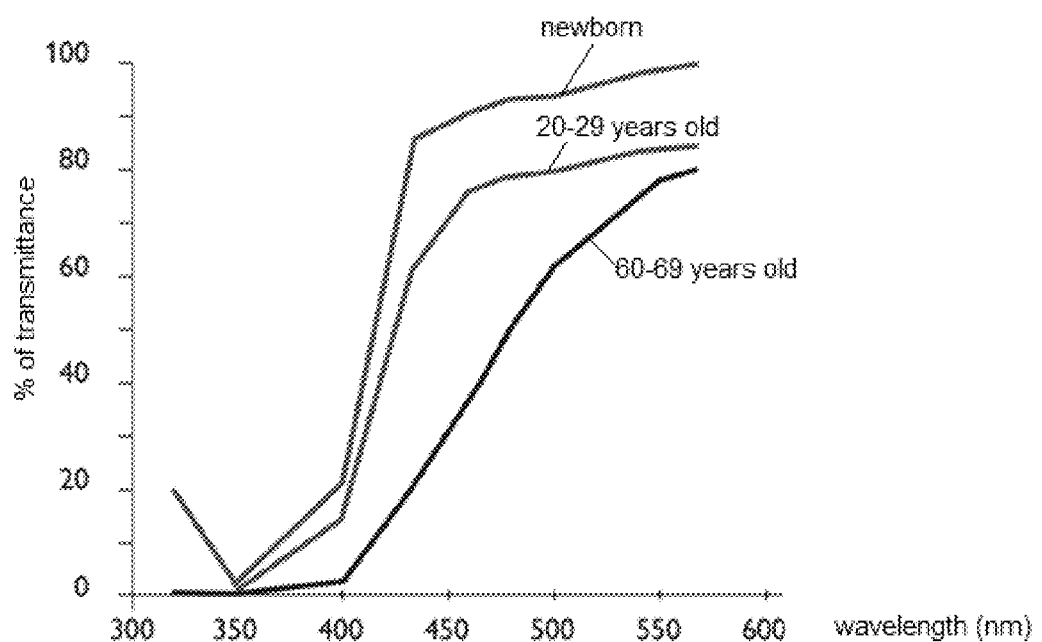
FIG. 2 shows a graph with the percentage of transmittance of the crystal lens according to that described in [BRAINARD, G. C. et al. "Action spectrum for melatonin regulation in humans: Evidence for a novel circadian photoreceptor", Journal of Neuroscience (2001)].
Figure 3A:
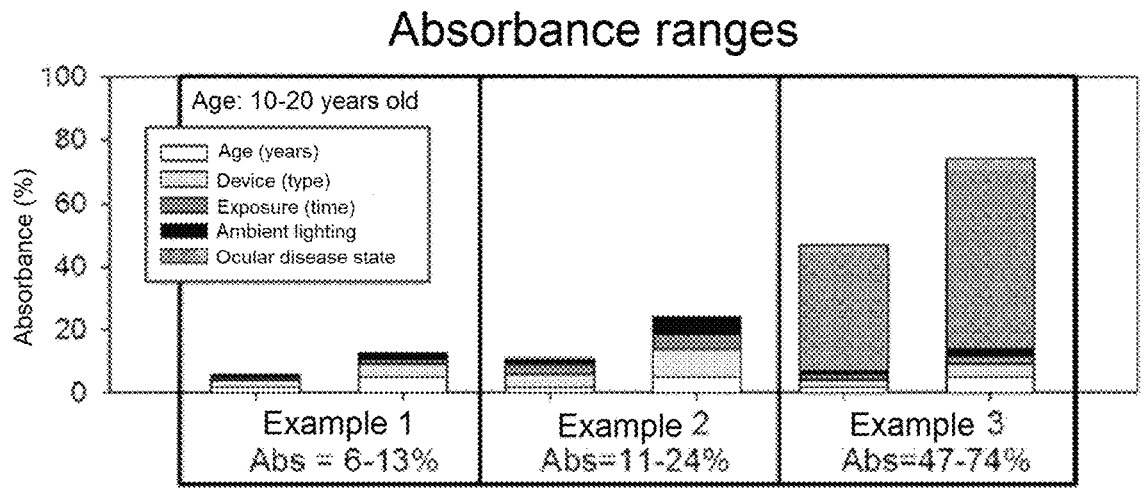
FIGS. 3a-3c shows the selective absorbance of the blocking element of short wavelengths between 380-500 nm of the present invention for three examples of people of different age: 25 years old (FIG. 3a), 45 years old (FIG. 3b) and 76 years old (FIG. 3c) according to the state of the art.
Figure 3B:
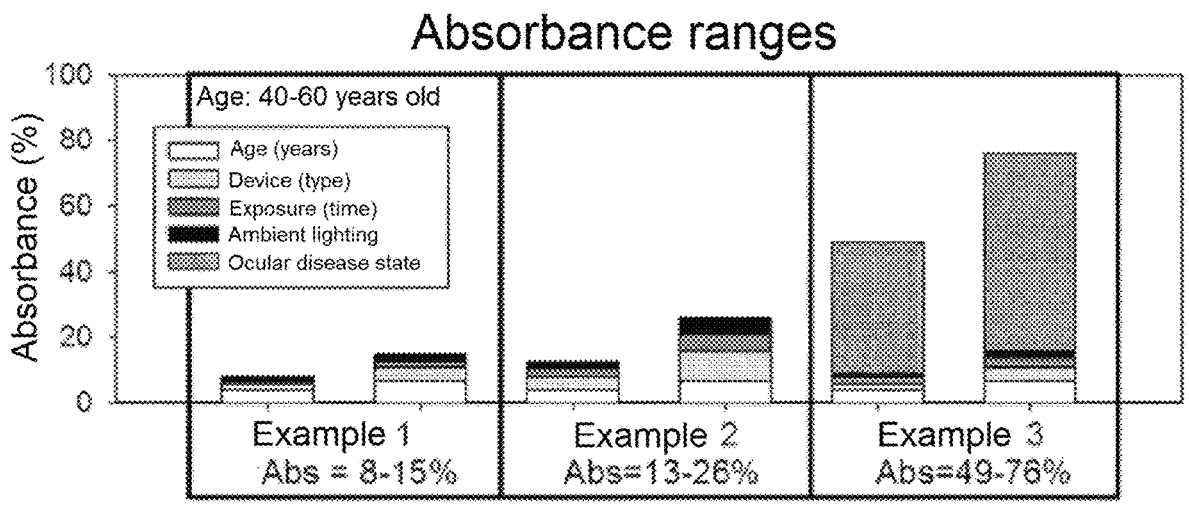
Figure 3C:
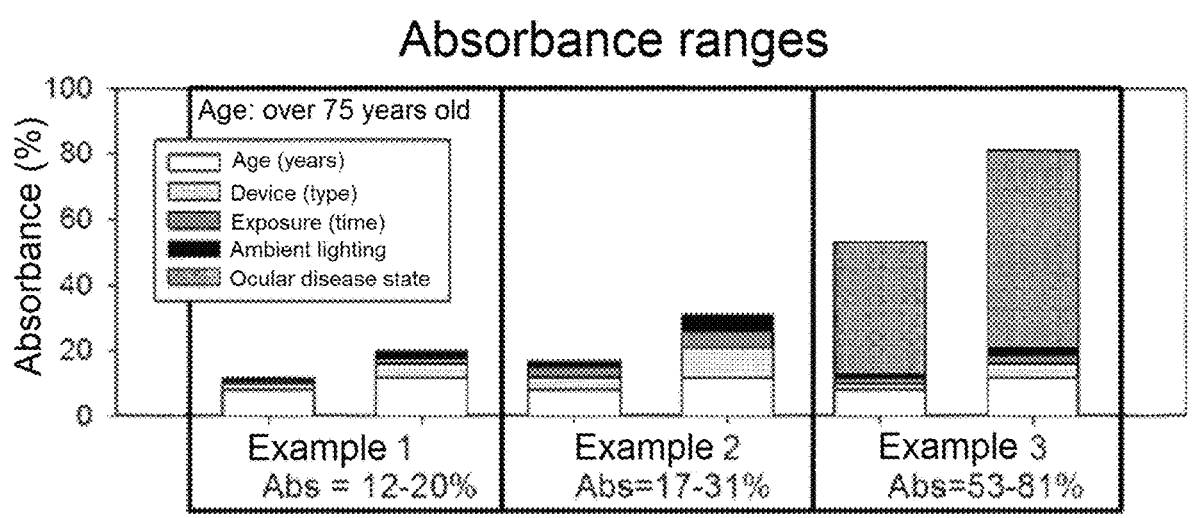
Figure 4:
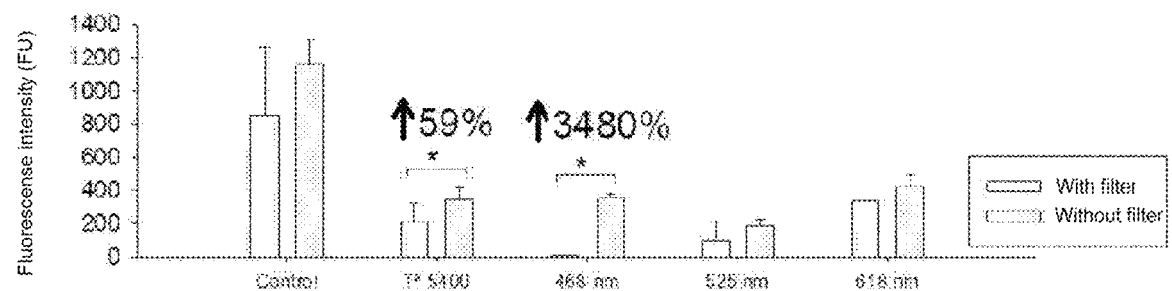
FIG. 4 shows a graph with the LED light effect and the photoprotective effect of a blocking element that selectively absorbs the short wavelengths between 380-500 nm on the cell viability, indicative of cell survival in human retinal pigment epithelial cells, according to the state of the art.
Figure 5:
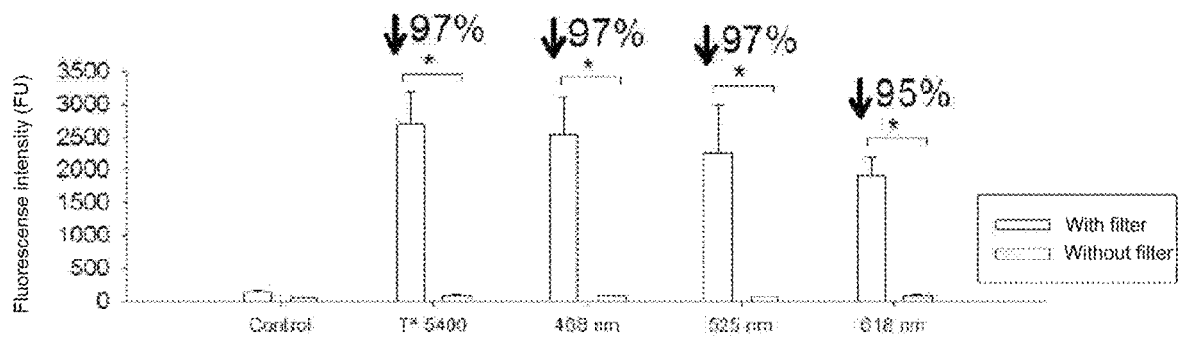
FIG. 5 shows the LED light effect and the photoprotective effect of a blocking element that selectively absorbs the short wavelengths between 380-500 nm on the activation of the human histone H2AX, indicative of DNA damage in human retinal pigment epithelial cells, according to the state of the art.
Figure 6:
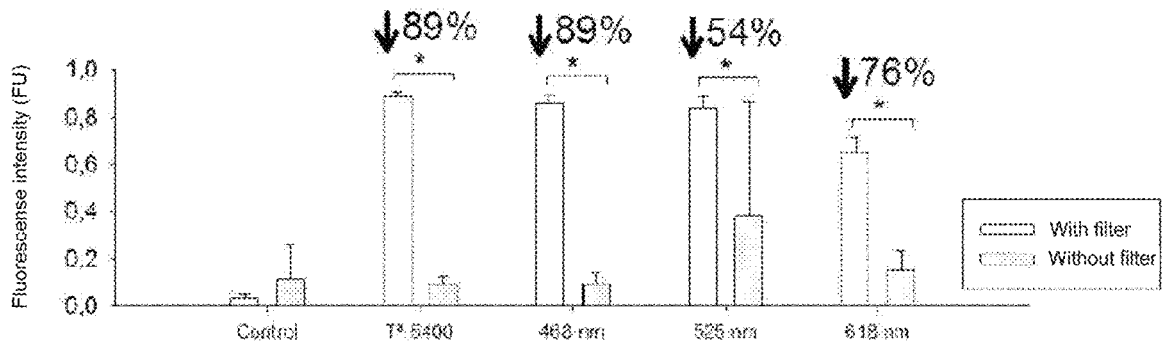
FIG. 6 shows the LED light effect and photoprotective effect of a blocking element that selectively absorbs the short wavelengths between 380-500 nm on the activation of the caspase-3, -7, indicative of apoptosis in human retinal pigment epithelial cells, according to the state of the art.

The present invention aims to a diopter for blocking short and medium wavelengths between 380-590 nm wherein the mitochondrial damage is very high, in combination with a diopter with short wavelengths ranging between 380-500 nm.

To evaluate the feasibility of the diopter, a test which consisted of two experiments has been established: a first experiment without diopter and a second experiment with diopter.

In the experiment without diopter, on the first day the cells of the retinal pigment epithelium (RPE) were seed in assay plates and on day 2 the photo-exposure was started. The photo-exposure device contained four LEDs, each in isolated compartments:

Blue LED—It emits light at the wavelength of 468 nm.
Green LED—It emits light at the wavelength of 525 nm.
Red LED—It emits light at the wavelength of 616 nm.
White LED—It emits in the visible spectrum at 5400° K.

Three photo-exposure cycles were carried out. Each cycle comprised 12 hours of photo-exposure followed by a recovery period of 12 hours. Prior to the photo-exposure, the source was pre-warmed for 15 minutes. Every day cells were added in fresh medium. The 5th day of the experiment the same was completed. Probes and antibodies were applied and the readings were carried out.

For the second experiment with diopter the first experiment methodology was followed but diopters were interposed between the light source and RPE cells. The diopters placed on the support that separates the cells from the light source followed the following order:

LIGHT SOURCE
DIOPTER WITH SHORT WAVELENGTHS (380-500 nm)
DIOPTER WITH MEDIUM WAVELENGTHS (500-590 nm)
TRANSPARENT UV FILTER
RPE CELLS

As indicated, a diopter is a surface separating two means with different refractive index. The diopters with short and medium wavelengths are therefore two independent diopters that, combined their effects, make up the diopter object of the invention in its most basic embodiment. The UV filter is not part of the present invention. On the other hand, its presence does not affect the study of the visible spectrum.

It has been proven that between the functions of the mitochondria highlights their participation in the mechanisms of cell death by apoptosis, where the permeabilization of mitochondrial outer membrane and the release of proteins important in the intermembrane space of the mitochondria are important characteristics that define this process. Specifically pro-apoptotic proteins such as cytochrome C, among others, are released during early stages of apoptosis.

Tetramethylrhodamine, methyl ester TMRM is a fluorescent cationic probe which, upon entering the cell, is quickly sequestered by mitochondria accumulating in a form negatively charged. The fluorescent signal emitted by this probe can be directly correlated with the mitochondrial inner membrane potential. Decrease of the fluorescence or its disappearance indicates the loss of integrity of the mitochondrial membrane, in definitive cell damage.

The toxicity experiment was conducted after the cells were incubated in the presence of light of different wavelength designed in the experiment, for 3 exposure/rest cycles of 12 hours per cycle. After incubation, cells were washed with PBS and the fluorescent probes TMRM added; to measure the mitochondrial membrane potential respectively. The probes were added at a concentration of 1:1000, for 30 minutes. Once the incubation is completed, the cells were washed with PBS and the fluorescence emitted by cells was read using a fluorescence microscope BD Pathway 855. The fluorescence produced by the probe TMRM (mitochondrial membrane potential) at 594 nm.

Figure 7:
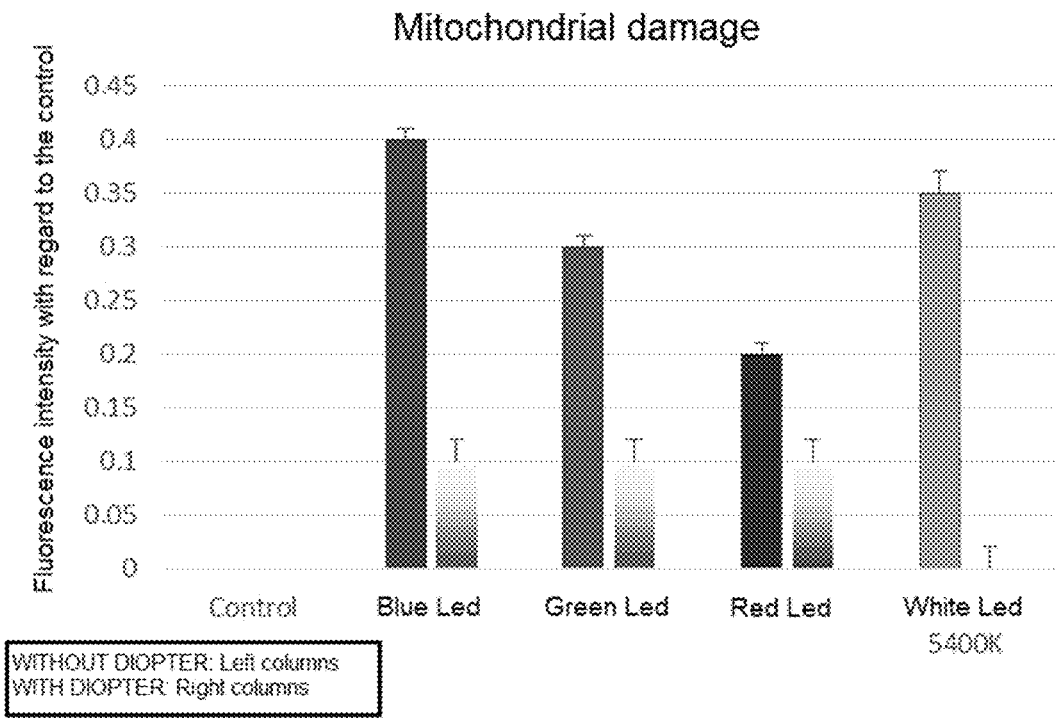
FIG. 7 shows a chart with the mitochondrial damage with and without diopter for blocking short wavelengths between 380-590 nm according to the present invention.

The results are shown in FIG. 7. This graph presents the bars that represent the fluorescence intensity, directly proportionally related to damage to the membrane. Percentages express the decrease of damage in membrane when the diopter is interposed.

For the calculation of the protective effect the results for each type of LED have normalized independently with respect to the damage obtained without diopter. Thus, mitochondrial damage detected in cells exposed without filter was considered as 100% of the damage that could be caused by a certain LED. The protective effect of the diopter is calculated as a percentage, based on cells that could suffer from phototoxic damage and having mitochondrial alterations.

For example, in the case of the blue LED, during the exposure without diopter, a mitochondrial damage of 0.4 is obtained, this considered as 100% (normalized to 1) of the damage that could be produced by the emission of this LED. By interposing the diopters, damage is reduced to 0.1, i.e., when interposing the diopters, only 25% of the cells suffer from mitochondrial alterations (compared to 75% of cells that do not suffer alterations). This means that the diopter prevent mitochondrial damage in 75% of the cases which, if it were not for the protection, cells undergo apoptosis process by mitochondrial damage.

Figure 8:
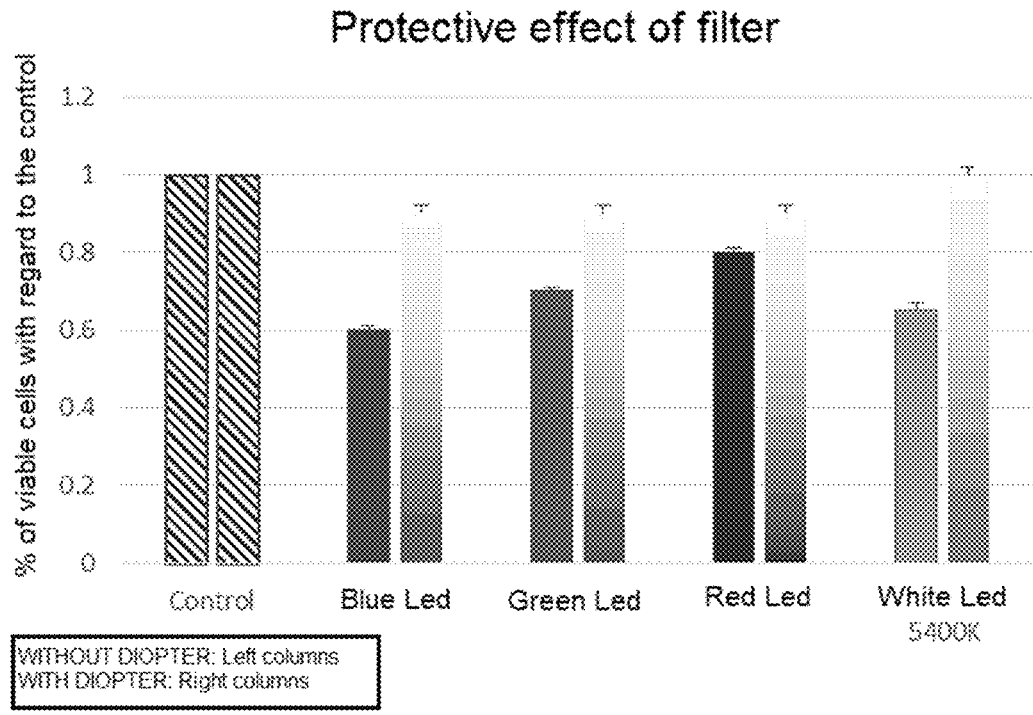
FIG. 8 shows a chart with the protective effect of the diopter with and without diopter for blocking short wavelengths between 380-590 nm according to the present invention.

FIG. 8 shows the protective effect of the diopter used in the test, where the bars represent the fluorescence intensity that represents the integrity of mitochondrial membrane. The percentages express the proportions of viable cells when the diopter is interposed. The percentages are normalized with respect to the control (i.e. cells without exposure).

As shown in the previous example, the simplest example of a diopter has been indicated according to the present invention consisting of:

a) a first diopter with a first pigment distributed on its surface
  a) where said first pigment has an optical density with a selective absorption of short wavelengths ranging from 380 nm and 500 nm between a maximum and minimum threshold of absorption; and b) a second diopter with a second pigment distributed on its surface
   a) where said second pigment has an optical density with a selective absorption of short wavelengths ranging from 500 nm and 590 nm between a maximum and minimum threshold of absorption.

Logically, the first and second pigment does not indicate an order, and may be mixed together, separated by layers or in any other way in which its effects are combined.

However, this is only one of the possible embodiments having the diopter, including embodiments by software, which allows blocking the range of desired short wavelengths (380-590 nm) without reducing widely the total intensity or total amount of light that emits the source, that in portable electronic devices is a display screen, usually of type LED.

In general, all embodiments must comply with a number of factors (table 5) to which a maximum and minimum weight is given to set, precisely, the maximum and minimum thresholds of absorbance for each individual or group of individuals (when they can be grouped). Some might think it is not necessary to have a maximum and minimum absorbance range and completely block the passage of the short and medium wavelengths between 380 and 590 nm. However, the total blocking of the blue light within these ranges produces effects both on the visibility through the diopter and on the individual's circadian cycle itself, so it is mandatory to set a minimum and maximum absorbance range without reaching a total blocking of the short and medium wavelengths. In addition, when specifying in an individualized or group way the thresholds it allows adjusting the optimal blocking of the short and medium wavelengths, thus allowing minimizing the negative effects on the display and the individual's circadian cycle.

In people with retinal pathology and/or older than 75 years, in situations that recommended absorption exceeds 75% for wavelengths between 380 and 590 nm it is recommended to add an attenuator from between 20-50% for the rest of the bands (590-700 nm), for television screens or for those screens that cannot regulate the emission intensity.

TABLE 5

| Factor | Degree | Maximum limit (%) | Minimum limit (%) |
|---|---|---|---|
| Age (years) | 0-9 | 10 | 4 |
|  | 10-19 | 9 | 5 |
|  | 20-39 | 9 | 5 |
|  | 40-59 | 12 | 6 |
|  | 60-79 | 15 | 7 |
|  | >79 | 20 | 10 |
| Type of used devices (working distance) | Smartphones (25-40 cm) | 5 | 2 |
|  | Tablets (25-40 cm) | 5 | 2 |
|  | Computer screens (41-70 cm) | 3 | 1 |
|  | Television screens (>70 cm) | 3 | 1 |
| Total exposure time (hours) | <3 | 4 | 3 |
|  | 3-5 | 5 | 4 |
|  | 6-8 | 6 | 5 |
|  | 9-10 | 7 | 5 |
|  | >10 | 7 | 5 |
| Conditions of lowest ambient lighting during the use of the devices (cd/m2) | Photopioc (>5) | 2 | 1 |
|  | Mesopic (0.005-5) | 5 | 2 |
|  | Scotopic (<0.005) | 10 | 4 |

TABLE 5-continued

| Factor | Degree | Maximum limit (%) | Minimum limit (%) |
|---|---|---|---|
| Disease State | Retinal disease states | | |
|  | Mild stage | 50 | 30 |
|  | Moderate stage | 60 | 40 |
|  | Severe stage | 70 | 50 |
|  | Corneal disease states | | |
|  | Mild stage | 20 | 10 |
|  | Moderate stage | 30 | 20 |
|  | Severe stage | 40 | 30 |
|  | Palpebral disease states | 8 | 5 |
|  | Conjunctival disease states | 8 | 5 |
|  | Scleral disease states | 8 | 5 |
|  | Glaucoma | 20 | 10 |
|  | Pseudophakic/ Aphakia | 30 | 10 |

The sum of the various factors listed by way of example in table 5 is what gives as a result a maximum and minimum absorbance threshold that allow maximizing the protection and minimizing the alterations in the circadian cycle and the display of the objects through the diopter.

Thus, for a 38-year-old user (maximum 9, minimum 5) that works with a computer (3/1), with an exposure time to the light source of more than 10 hours (7/5), with an ambient lighting of the place where the user interacts with the photopic LED-type light source (2/1) and without disease states, it is stated that we would have a maximum absorbance in the range of 380-500 nm of (9+2+3+7) of 21%, while the minimum of absorbance would be 12%. However, if the same individual uses various electronic devices (computer, tablet and Smartphone) for more than 10 hours in environments of high and low lighting, the preferred absorbance range will vary by 10% for the maximum and by 4% for the minimum. On the other hand, if the individual has a moderate retinal disease state and was exposed to television for 3-5 hours a day in high light conditions, the recommended absorbance range will also vary according to the sum indicated.

Examples and practical embodiments to achieve this selective absorbance vary since it can be a multilayer substrate (such as the external blocking element of a LED display), a coating (gel, foam, emulsion, solution, dilution or mixture) with a pigment of an optical density, or reduction via software of the emission on the spectrum of 380-590 nm.

A diopter is also one selected among: intraocular lens, contact lens, ophthalmic lens, a filter in windows of buildings and/or vehicles, a solar lens with and/or without mirrored surface, a lens for welding protection or an intermediate layer inserted in a display screen and configured to block emissions in short and medium wave lengths comprised between 380-590 nm.

In all these cases we are in the same situation as in the diopter described, i.e., including a pigment for blocking medium wavelengths in addition to a pigment for blocking short wavelengths, so as to obtain a result similar to that described in the tests.

According to the results reported in the tests of FIGS. 7-8, is demonstrated that the reduction of the emission caused by light sources as those incorporated in the display screens of mobile devices (typically, but not exclusively, of type LED) in the spectrum comprised between the 380-590 nm is beneficial, thus solving the technical problem described previously.

In all the previous embodiments, a second diopter is included for medium wavelengths ranging from 500 nm and 590 nm reducing the effect of the medium wavelengths in the range of the green which, as indicated, has a very high range of cell death.

Figure 9:
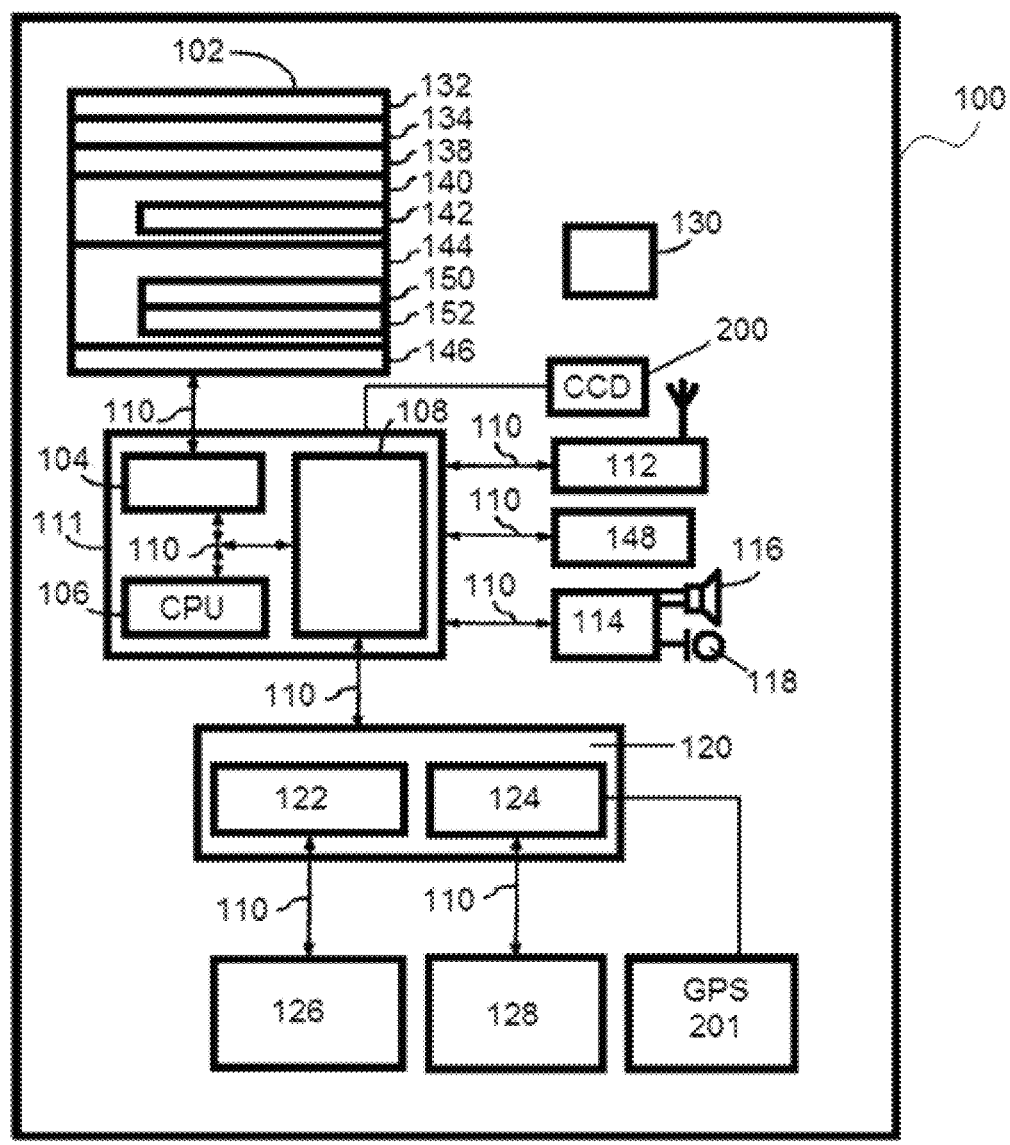
FIG. 9 shows a scheme of a portable electronic device as that used in the present invention.

Following is a practical example of embodiment of a portable electronic device (100) as one that can be used in the present invention according to some practical embodiments is shown in FIG. 9. More specifically, the portable electronic device 100 of the invention includes a memory 102, a memory controller 104, one or more processing units (CPU) 106, a peripherals interface 108, a RF circuitry 112, an audio circuitry 114, a speaker 116, a microphone 118, an input/output (I/O) subsystem 120, a screen 126, preferably of LED type, without excluding other practical embodiments, other input or control devices 128, and an external port 148. These components communicate over the one or more communication buses or signal lines 110. The device 100 can be any portable electronic device, including but not limited to a handheld computer, a tablet computer, a mobile phone, a media player, a personal digital assistant (PDA), or the like, including a combination of two or more of these items. It should be appreciated that the device 100 is only one example of a portable electronic device 100, and that the device 100 may have more or fewer components than shown, or a different configuration of components. The various components shown in FIG. 1 may be implemented in hardware, software or a combination of both hardware and software, including one or more signal processing and/or application specific integrated circuits. In the same way, the display 126 has been defined as a LED display, although the invention may also be implemented in devices with a standard display.

The memory 102 may include high speed random access memory and may also include non-volatile memory, such as one or more magnetic disk storage devices, flash memory devices, or other non-volatile solid state memory devices. In some embodiments, the memory 102 may further include storage remotely located from the one or more processors 106, for instance network attached storage accessed via the RF circuitry 112 or external port 148 and a communications network (not shown) such as the Internet, intranet(s), Local Area Networks (LANs), Wide Local Area Networks (WLANs), Storage Area Networks (SANs) and the like, or any suitable combination thereof. Access to the memory 102 by other components of the device 100, such as the CPU 106 and the peripherals interface 108, may be controlled by the memory controller 104.

The peripherals interface 108 couples the input and output peripherals of the device to the CPU 106 and the memory 102. The one or more processors 106 run various software programs and/or sets of instructions stored in the memory 102 to perform various functions for the device 100 and process data.

In some embodiments, the peripherals interface 108, the CPU 106, and the memory controller 104 may be implemented on a single chip, such as a chip 111. In some other embodiments, they may be implemented on separate chips.

The RF (radio frequency) circuitry 112 receives and sends electromagnetic waves. The RF circuitry 112 converts electrical signals to/from electromagnetic waves and communicates with communications networks and other communications devices via the electromagnetic waves. The RF circuitry 112 may include well-known circuitry for performing these functions, including but not limited to an antenna system, an RF transceiver, one or more amplifiers, a tuner, one or more oscillators, a digital signal processor, a CODEC chipset, a subscriber identity module (SIM) card, memory, and so forth. The RF circuitry 112 may communicate with the networks, such as the Internet, also referred to as the World Wide Web (WWW), an Intranet and/or a wireless network, such as a cellular telephone network, a wireless local area network (LAN) and/or a metropolitan area network (MAN), and other devices by wireless communication. The wireless communication may use any of a plurality of communications standards, protocols and technologies, including but not limited to Global System for Mobile Communications (GSM), Enhanced Data GSM Environment (EDGE), wideband code division multiple access (W-CDMA), code division multiple access (CDMA), time division multiple access (TDMA), Bluetooth, Wireless Fidelity (Wi-Fi) (e.g., IEEE 802.11a, IEEE 802.11b, IEEE 802.11g and/or IEEE 802.11n), voice over Internet Protocol (VoIP), Wi-MAX, a protocol for email, instant messaging, and/or Short Message Service (SMS), or any other suitable communication protocol, including communication protocols not yet developed as of the filing date of this document.

The audio circuitry 114, the speaker 116, and the microphone 118 provide an audio interface between a user and the device 100. The audio circuitry 114 receives audio data from the peripherals interface 108, converts the audio data to an electrical signal, and transmits the electrical signal to the speaker 116. The speaker converts the electrical signal to human-audible sound waves. The audio circuitry 114 also receives electrical signals converted by the microphone 116 from sound waves. The audio circuitry 114 converts the electrical signal to audio data and transmits the audio data to the peripherals interface 108 for processing. Audio data may be may be retrieved from and/or transmitted to the memory 102 and/or the RF circuitry 112 by the peripherals interface 108. In some embodiments, the audio circuitry 114 also includes a headset jack (not shown). The headset jack provides an interface between the audio circuitry 114 and removable audio input/output peripherals, such as output-only headphones or a headset with both output (headphone for one or both ears) and input (microphone).

The I/O subsystem 120 provides the interface between input/output peripherals on the device 100, such as the LED display 126 and other input/control devices 128, and the peripherals interface 108. The I/O subsystem 120 includes a LED-display controller 122 and one or more input controllers 124 for other input or control devices. The one or more input controllers 124 receive/send electrical signals from/to other input or control devices 128. The other input/control devices 128 may include physical buttons (e.g., push buttons, rocker buttons, etc.), dials, slider switches, and/or geographical location means 201, such as GPS or similar.

In this practical embodiment, the LED display 126 provides both an output interface and an input interface between the device and a user. The LED-display controller 122 receives/sends electrical signals from/to the LED display 126. The LED display 126 displays visual output to the user. The visual output may include text, graphics, video, and any combination thereof. Some or all of the visual output may correspond to user-interface objects, further details of which are described below.

The LED display 126 also accepts input from the user based on haptic contact. The LED display 126 forms a touch-sensitive surface that accepts user input. The LED display 126 and the LED-display controller 122 (along with any associated modules and/or sets of instructions in the memory 102) detects contact (and any movement or break of the contact) on the LED display 126 and converts the detected contact into interaction with user-interface objects, such as one or more soft keys, that are displayed on the LED display. In an exemplary embodiment, a point of contact between the LED display 126 and the user corresponds to one or more digits of the user.

The LED display 126 is or may be formed by a plurality of light-emitter diodes, and more specifically formed by white LEDs, although other type of LED emitters may be used in other embodiments.

The LED display 126 and LED-display controller 122 may detect contact and any movement or break thereof using any of a plurality of touch sensitivity technologies, including but not limited to capacitive, resistive, infrared, and surface acoustic wave technologies, as well as other proximity sensor arrays or other elements for determining one or more points of contact with the LED display 126.

The device 100 also includes a power system 130 for powering the various components. The power system 130 may include a power management system, one or more power sources (e.g., battery, alternating current (AC)), a recharging system, a power failure detection circuit, a power converter or inverter, a power status indicator (e.g., a light-emitting diode (LED)) and any other components associated with the generation, management and distribution of power in portable devices.

In some embodiments, the software components include an operating system 132, a communication module (or set of instructions) 134, a contact/motion module (or set of instructions) 138, a graphics module (or set of instructions) 140, a user interface state module (or set of instructions) 144, and one or more applications (or set of instructions) 146.

The operating system 132 (e.g., Darwin, RTXC, LINUX, UNIX, OS X, WINDOWS, or an embedded operating system such as VxWorks) includes various software components and/or drivers for controlling and managing general system tasks (e.g., memory management, storage device control, power management, etc.) and facilitates communication between various hardware and software components.

The communication module 134 facilitates communication with other devices over one or more external ports 148 and also includes various software components for handling data received by the RF circuitry 112 and/or the external port 148. The external port 148 (e.g., Universal Serial Bus (USB), FIREWIRE, etc.) is adapted for coupling directly to other devices or indirectly over a network (e.g., the Internet, wireless LAN, etc.).

The contact/motion module 138 detects contact with the LED display 126, in conjunction with the LED-display controller 122. The contact/motion module 138 includes various software components for performing various operations related to detection of contact with the LED display 122, such as determining if contact has occurred, determining if there is movement of the contact and tracking the movement across the LED display, and determining if the contact has been broken (i.e., if the contact has ceased). Determining movement of the point of contact may include determining speed (magnitude), velocity (magnitude and direction), and/or an acceleration (including magnitude and/or direction) of the point of contact. In some embodiments, the contact/motion module 126 and the LED display controller 122 also detects contact on the LED pad.

The graphics module 140 includes various known software components for rendering and displaying graphics on the LED display 126. Note that the term "graphics" includes any object that can be displayed to a user, including without limitation text, web pages, icons (such as user-interface objects including soft keys), digital images, videos, animations and the like.

In some embodiments, the graphics module 140 includes an optical intensity module 142. The optical intensity module 142 controls the optical intensity of graphical objects, such as user-interface objects, displayed on the LED display 126. Controlling the optical intensity may include increasing or decreasing the optical intensity of a graphical object. In some embodiments, the increase or decrease may follow predefined functions.

The user interface state module 144 controls the user interface state of the device 100. The user interface state module 144 may include a lock module 150 and an unlock module 152. The lock module detects satisfaction of any of one or more conditions to transition the device 100 to a user-interface lock state and to transition the device 100 to the lock state. The unlock module detects satisfaction of any of one or more conditions to transition the device to a user-interface unlock state and to transition the device 100 to the unlock state.

The one or more applications 130 can include any applications installed on the device 100, including without limitation, a browser, address book, contact list, email, instant messaging, word processing, keyboard emulation, widgets, JAVA-enabled applications, encryption, digital rights management, voice recognition, voice replication, location determination capability (such as that provided by the global positioning system (GPS)), a music player (which plays back recorded music stored in one or more files, such as MP3 or AAC files), etc.

In some embodiments, the device 100 may include one or more optional optical sensors (not shown), such as CMOS or CCD image sensors, for use in imaging applications.

The portable electronic device (100) comprising a screen (126); one or more processors (106); a memory (102); and one or more programs wherein the program(s) (132 to 146) are stored in the memory (102) and configured to be executed by at least the processor(s) (106), the programs (132 to 146) including instructions to: calculate a maximum and minimal threshold of the emissions of short wavelengths between 380 and 590 nm; selectively reduce the emission of short and medium wavelengths between 380-590 nm of the lighting sources contained in the screen (126) by modifying the colors in the operating system or in the color intensity module (142). All of this as has already been indicated above.

The portable electronic device (100) can be fixed in other embodiments. In other embodiments the LED display (126) may be any screen which emits light in the visible range (RGB).

The selective reduction is carried out by modifying the colors in the operating system (134) or in the color intensity module (142). In any case, there is also the possibility that said selective reduction is temporarily progressive so that the greater exposure time to the screen (126) of device (100), the greater reduction will be. The change in colors in the operating system (134) can be automated through an application that after the questions to the user described in table 5 or setting by any other method the data necessary to calculate the maximum and minimum threshold for that individual on that mobile device and act on the RGB control of the O.S. (134) so that said emissions are reduced. The latter can also be made in the color intensity module, reducing the intensity or brightness.

Finally, the software product with instructions configured for execution by one or more processors that, when executing by a portable electronic device (100) as described above, make said device (100) to carry out the computer-implemented method to block the short and medium wavelengths in light sources characterized in that it comprises the steps of: (i) calculating the emissions of short and medium wavelengths between 380 and 590 nm; and (ii) selectively reducing the emission of short and medium wavelengths between 380-590 nm of the LEDs contained in the screen (126) depending on the calculation set out in the step (i).

It is also obvious to a person skilled in the art that the electronic device can be portable as in the described embodiment, or fixed, provided that it comprises the basic elements described to execute its functionality, regardless of whether any of its parts is executed on local or remotely, via communication network. For example, the software product can be run in a client-server architecture so that emissions can be regulated by a physician, through application of telemedicine.

The calculation of the emissions is a function of at least one of the following variables: age of a user of LED-type light source, separation distance to the LED-type light source, size of the LED-type light source, exposure time to the light source by the user, ambient lighting of the place where the user interacts with the LED-type light source and the possible retinal and/or corneal disease state.

The benefits of the invention in its embodiment in an electronic device are multiple, as well as their applications. For example, its use is beneficial to improve the quality of life of the user in different everyday situations, for example: not affecting the metabolism of the users or their meal plan; notifying the user of overuse in contrast to the hours of sleep; notifying an intensive use of the macula, i.e. an excessive concentration on the device, for example, due to an excess of hours of reading, which may imply a reduction of the emissions depending on the hours of reading, to compensate them; improvement in concentration and performance tasks; very low lighting night environments, emissions are reduced by regulating the circadian cycle, which also results in the mood of the user; or finally detecting if it is a child to reduce emissions or block the portable electronic device.

This software product can be physically implemented in the display hardware itself or in the video controller of any computer system comprising a display.

The protection of the retina, cornea and crystalline of the harmful action of the short wavelengths, as well as the elimination of the eyestrain, the improvement of the comfort and visual function, and the avoidance of the insomnia, final objects of the invention, are also achieved both with the computer-implemented method and with the electronic device (100), and with the described computer product.

One of the possibilities given by the invention is the possibility of changing the background of any document to one less aggressive for the human eye. Indeed, today, most of the documents have a white background, while its content is typically in a color that offers a strong contrast, like black, blue, red or green. This is conditioned by the fact that electronic documents, in general, try to imitate the documents written on paper, in addition to minimize the cost of printing of said documents.

Another possibility granted by the invention is that in the case of exposures to short and medium wavelengths are intermittent or divided, the exposure to screen can be managed per time-points. Similarly, it can be set a progression in the illumination of the screen from the beginning of the lighting until a threshold established for each user is reached depending on the time of day and user's sleep states, which affect the circadian cycle and the regulation of melatonin.

However, that contrast, as described, implies a strong light emission with a harmful content for the human eye. Therefore, and thanks to the described method, the computer-implemented method, the device, and the computer product implement a further step of detecting the background of the document shown to the user, and a second step of switching said background to one with a reduced emission on the spectrum indicated.

Finally, it should be noted that the invention can be used on any LED device, including OLED devices. An OLED consists of two thin organic layers: an emission layer and a conducting layer, which at the same time are comprised between a thin film acting as an anode and another identical one acting as a cathode. In general, these layers are made of molecules or polymers that conduct electricity. Their electrical conductivity levels are between the level of an insulator and that of a conductor, and for this reason they are called organic semiconductors. The choice of organic materials and the structure of the layers determine the operating characteristics of the device: emitted color, time life and energy efficiency. For example, this structure may be modified to incorporate a diopter such as that of the invention in such a way that it comprises a layer or pigmented substrate that blocks the short- and medium-wave radiations ranging between 380-590 nm according to the stated embodiments of the invention.

The present invention is also useful in screens of large dimensions of type RGB, where it can be used to selectively block the short and medium wavelengths ranging between 380-590 nm.

What is claimed is:

1. An electronic device comprising:
   a display;
   a memory;
   a processor coupled to the memory and configured to:
   determine, by detection or an input of a user, at least one factor comprising:
     total time a user is exposed to the display during use of the electronic device, ambient lighting of a place where the user interacts with the display, or a time of day the display is operating;
   obtain, for each of the at least one factor, a maximum percent of reduction and a minimum percent of reduction for a light emission of the display within a light spectrum between 380 nm and 590 nm, by extracting the maximum percent of reduction and the minimum percent of reduction corresponding to each of the at least one factor from a predetermined look-up table; and
   reduce, based upon the obtained values, an intensity of the light emission of the display within the light spectrum between 380 nm and 590 nm, wherein a percent reduction is between the sum of each determined maximum percent of reduction and the sum of each determined minimum percent of reduction.

2. The device of claim 1, wherein the reduction of the intensity of light emission of the display between the maximum and minimum percent of reduction only within the light spectrum between 380 nm and 590 nm is performed by reducing at least a percentage of the light spectrum emitted from the display.

3. The device of claim 1, wherein the reduction of the intensity of light emission of the display between the maximum and minimum percent of reduction only within the light spectrum between 380 nm and 590 nm is variable.

4. The device of claim 1, wherein the reduction of the intensity of light emission is progressive between the minimum and maximum percent of reduction.

5. The device of claim 1, wherein the reduction of the intensity of light emission is within discrete portions of the display.

6. The device of claim 1, wherein the reduction of the intensity of light emission of the display is further based upon the display producing less light emission within the light spectrum emitted from the display.

7. The device of claim 1, wherein the reduction of the intensity of the display is temporarily progressive depending on the exposure time of the user.

8. The device of claim 1, wherein the processor is further configured to:
detect a background of an electronic document viewed by the user of the electronic device, and
switch the background of the electronic document viewed by the user to a background with a reduced emission in the light spectrum between 380 nm and 590 nm.

9. The device of claim 1, wherein the processor is further configured to determine, by detection or a user input, a plurality of factors further comprising: input of an age of the user of the electronic device.

10. The device of claim 1, wherein the processor is further configured to determine a working distance between the user and the display.

11. The device of claim 1 wherein the processor is further configured to determine a size of the display.

12. A computer-implemented method for blocking short and medium wavelength radiations that damage the visual system comprising the steps of:
determining, by detection or an input of a user, at least one factor comprising:
total time a user is exposed to a display during use of an electronic device, ambient lighting of a place where the user interacts with the display, or a time of day the display is operating,
obtaining, for each of the at least one factor, a maximum percent of reduction and a minimum percent of reduction for a light emission of the display within a light spectrum between 380 nm and 590 nm, by extracting the maximum percent of reduction and the minimum percent of reduction corresponding to each of the at least one factor from a predetermined look-up table, and
reducing, based upon the obtained values, an intensity of the light emission of the display within the light spectrum between 380 nm and 590 nm, wherein a percent reduction is between the sum of each determined maximum percent of reduction and the sum of each determined minimum percent of reduction.

13. The method of claim 12, wherein the reduction of the intensity of light emission of the display between the maximum and minimum percent of reduction only within the light spectrum between 380 nm and 590 nm is performed by reducing at least a percentage of the light spectrum emitted from the display.

14. The method of claim 12, wherein the reduction of the intensity of light emission of the display between the maximum and minimum percent of reduction only within the light spectrum between 380 nm and 590 nm is variable.

15. The method of claim 12, wherein the reduction of the intensity of light emission is progressive between the minimum and maximum percent of reduction.

16. The method of claim 12, wherein the reduction of the intensity of light emission is within discrete portions of the display.

17. The method of claim 12, wherein the reduction of the intensity of light emission of the display is further based upon the display producing less of light emission within the light spectrum between 380 nm and 590 nm.

18. The method of claim 12, wherein the reduction of the intensity of the display is temporarily progressive depending on the exposure time of the user and the time of the day.

19. The method of claim 12, further comprising:
detecting a background of an electronic document viewed by the user of the electronic device, and
switching the background of the electronic document viewed by the user to a background with a reduced emission in the light spectrum between 380 nm and 590 nm.

20. The method of claim 12, further comprising receiving an age of the user of the electronic device.

21. The method of claim 12, further comprising determining a working distance between the user and the display.

22. The method of claim 12, further comprising determining a size of the display.

* * * * *